(12) United States Patent
Zhang et al.

(10) Patent No.: US 7,528,298 B2
(45) Date of Patent: *May 5, 2009

(54) ENHANCED POLLENIZER AND METHOD FOR INCREASING SEEDLESS WATERMELON YIELD

(75) Inventors: Xingping Zhang, Woodland, CA (US); Thomas Vare Williams, Naples, FL (US)

(73) Assignee: Syngenta Participations AG (CH)

( * ) Notice: Subject to any disclaimer, the term of this patent is extended or adjusted under 35 U.S.C. 154(b) by 313 days.

This patent is subject to a terminal disclaimer.

(21) Appl. No.: 10/933,791

(22) Filed: Sep. 3, 2004

(65) Prior Publication Data

US 2005/0050597 A1 Mar. 3, 2005

Related U.S. Application Data

(63) Continuation-in-part of application No. 10/349,509, filed on Jan. 22, 2003, now Pat. No. 7,071,374, which is a continuation-in-part of application No. 10/091,154, filed on Mar. 5, 2002, now Pat. No. 6,759,576.

(51) Int. Cl.
*A01H 5/00* (2006.01)
*A01H 5/10* (2006.01)
*A01H 5/08* (2006.01)
*A01H 5/12* (2006.01)

(52) U.S. Cl. ...................................... 800/308; 800/298
(58) Field of Classification Search .................. 800/308
See application file for complete search history.

(56) References Cited

U.S. PATENT DOCUMENTS

| 5,007,198 A | 4/1991 | Gray et al. ................... 800/268 |
| 6,355,865 B1 | 3/2002 | Elmstrom ................... 800/308 |
| 6,759,576 B2 * | 7/2004 | Zhang et al. ................. 800/308 |
| 2003/0121075 A1 | 6/2003 | Barham |
| 2003/0163852 A1 | 8/2003 | Barham et al. |
| 2006/0168701 A1 | 7/2006 | Zhang ........................ 800/308 |

FOREIGN PATENT DOCUMENTS

WO WO 00/70933 11/2000

OTHER PUBLICATIONS

Poole. J. Heredity 35: 122-128, 1944.*
Porter (Hilgardia 10(12): 489-509, 1937.*
Crall et al, *SSDL: A High-quality Icebox Watermelon Breeding Line Resistant to Fusarium Wilt and Antracnose HortScience*, vol. 29, No. 6 (Jun. 1994), pp. 707-708.
Hochmuth, et al. "Cultural Management." in Maynard, D.N., *Watermelons: Characteristics, Production, and Marketing* (Virginia, ASHA Press, 2001), pp. 78-97.
Kenny, I.J. and Porter, D.R., *Relative Rind Toughness Among Watermelon Varieties* American Society for Horticultural Science, vol. 38 (1941) pp. 537-540.
*Known-You Seed*, (Kaohsiung, Taiwan), [catalog], 1991/1992, pp. 22.
*Known-You Seed*, (Kaohsiung, Taiwan), [catalog], 1994, pp. 2.
Maynard et al, *Triploid watermelon production practices and varieties Acta Horticulture*, vol. 318, (1992), pp. 169-178.
NeSmith, D.S. and Duval, J.R., *Fruit Set of Triploid Watermelons as a Function of Distance from a Diploid Pollinizer HortScience*, vol. 36(1) (Feb. 2001) pp. 60-61.
Poole, C.F., Genetics of Cultivated Cucurbits *The Journal of Heredity*, vol. 35 (1944) pp. 122-128.
Porter, D.R., *Inheritance of Certain Fruit and Seed Characters in Watermelons Hilgardia*, vol. 12, No. 10 (Jan. 1937) pp. 489-509.
Rhodes, B. and Dane, F, *Gene List for Watermelon Cucurbit Genetics Cooperative Report*, vol. 22 (1999) pp. 61-77.
United States Department of Agriculture, Insect Pollination of Cultivated Crop Plants, Common Vegetables for Seed & Fruit; Watermelon and Cirton [online]. Originally pubished 1976 [retrieved from the Internet: <URL: http://gears.tucson.ars.ag.gov/book/.
Wagner Force Measurement Instruments, [catalogue] [online]. [Internet: <URL: http://www.wagnerinstruments.com/] retrieved Jan. 13, 2004.
Wagner Force Measurement Instruments, [online manual]. [Internet: <URL: http://www.wagnerforce.com/manuals/ftmanual.pdf] retrieved Jan. 13, 2004.
Wolf et al., *Genetic Variability in Flower Attractiveness to Honeybees (Apis mellifera L.) within the Genus Citrullus HortScience*, vol. 34(5), (1999) pp. 860-863.
Gabriele Gusmini and Todd C. Wehner, "Foundations of Yield Improvement in Watermelon," *Crop Sci.*, 45, pp. 141-146 (2005).
John M. Poehlman and David A. Sleper, "Quantitative Inheritance," In Breeding Field Crops, 4th ed., Iowa State University Press, Ames, p. 71, (1995).
Buttrose et al., Some effects of Light Intensity Day Length and Temperature on Growth of Fruiting and Nonfruiting Watermelon Citrullus-Lanatus *Annals of Botany*, vol. 42, No. 179 (1978) pp. 599-608.
Fan Min et al., Identification of quantitative trait loci associated with fruit traits in watermelon (*Citullus lanantus* (*Thanb*) *Mansf*) and analysis of their genetic effects *Acta Genetica Sinica*, vol. 27, No. 10 (2000) pp. 901-910.

(Continued)

*Primary Examiner*—David H Kruse
*Assistant Examiner*—Keith O. Robinson
(74) *Attorney, Agent, or Firm*—S. Matthew Edwards (57) ABSTRACT

An enhanced, diploid pollenizer watermelon plant and method used to maximize the yield of triploid seedless watermelons per area. The enhanced pollenizer watermelon plant of the invention is either a hybrid variety, an open-pollinated variety or a synthetic variety, that exhibits the characteristics of small leaves and fruit with a brittle rind that splits when the fruit is overripe or breaks when relatively small physical forces are applied. In one embodiment, the watermelon plant of the invention is also characterized by extended flowering duration, thereby increasing the number of triploid watermelon flowers that are pollinated and set fruit. The method for producing a seedless watermelon fruit, includes the steps of providing a pollenizer diploid watermelon plant, extending the duration of flowering of the pollenizer plant while reducing the number of such plants needed to pollinate the same number of triploid watermelon plants, and maximizing dispersal of the pollenizer watermelon plant throughout the field of triploid watermelon plants.

5 Claims, 2 Drawing Sheets

OTHER PUBLICATIONS

Hegde, D.M., Physiological Analysis of Growth and Yield of Watermelon (*Citrullus lanatus Thunb Musf*) in Relation to Irrigation and Nitrogen Fertilization *Journal of Agronomy & Crop Science*, vol. 160 (1988) pp. 296-302.

Kano et al., Effects of summer day-time temperature on sugar content in several portions of watermelon fruit (*Citrullus lanatus*) *Journal of Horticultural Science & Biotechnology*, vol. 79, No. 1 (Jan. 2004) pp. 142-145.

Karchi et al., The importance of cultural practices in materializing yield potential in a tetraploid watermelon cultivar *Cucurbit Genetics Cooperative Report*, No. 6 pp. 59-61, 1983.

Scott et al., *Calcium Fertilization and Cultivar Affect Watermelon Rind Thickness and Resiliency Hortscience*, vol. 25, No. 9, (1990) pp. 1075.

Sugiyama et al., Relationship between Rind Hardness and Rind Tissue Structure in Watermelon *Journal of Japanese Society for Horticultural Science*, vol. 68, No. 1 (Jan. 1999) pp. 108-116.

Sundstrom et al., Influence of Potassium and Calcium on Quality and Yield of Watermelon Citrullus-Lanatus Cultivar Calhoun-Gray *Journal of the American Society for Horticultural Science*, vol. 108, No. 5 (1983) pp. 879-881.

Susin et al. *Fertility and Pollen Tube Growth in Polyploid Melons* (*Cucumis melo* L.), vol. 93 (1997) pp. 369-373.

* cited by examiner

ENHANCED POLLENIZER AND METHOD FOR INCREASING SEEDLESS WATERMELON YIELD

CROSS-REFERENCE TO RELATED APPLICATIONS

This application is a continuation-in-part of U.S. application Ser. No. 10/349,509, filed Jan. 22, 2003, which is a continuation-in-part of U.S. application Ser. No. 10/091,154, filed Mar. 5, 2002, now U.S. Pat. No. 6,759,576. The aforementioned applications are incorporated herein by reference in their entireties.

FIELD OF THE INVENTION

This invention is in the field of watermelon breeding, specifically relating to diploid watermelons used to pollinate triploid watermelon plants for the commercial production of seedless watermelon fruit, and includes a novel method for the production of triploid watermelon fruit.

BACKGROUND OF THE INVENTION

Watermelon is an important horticultural crop that accounts for 2% of the world area devoted to vegetable crops. There were 6,024,000 acres of watermelon grown in the world and 187,000 acres of watermelons grown in the United States in 1997 (FAO Production Yearbook 51, 1998). The estimated annual world watermelon value exceeded $7.6 billion when using the United States average price for 1995-1997. The United States watermelon crop amounted to over 41 million cwt, from over 174,000 harvested acres, and a farm value of over $266 million, accounted for 9.2% of the harvested acres, 10.0% of the production, and 3.5% of the value of the United States fresh vegetable industry in 1999 (USDA Agricultural Statistics 2001). California was the leading state in watermelon farm gate value, exceeded $72 million in 2000, due to high percentage of triploid seedless watermelon grown in California. Seedless watermelon receives well above the average price for seeded watermelons in the market.

The goal of plant breeding is to combine in a single variety or hybrid various desirable traits. Desirable traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, and maturity, are important. Other desired traits may include particular nutrient content, color, fruit shape, as well as taste characteristics.

As with many different plants, watermelon contains a fruit part and a plant part. Each part contains different traits that are desired by consumers and/or growers, including such traits as flavor, texture, disease resistance, and appearance traits such as shape and color. The seedless trait in the watermelon fruit is highly desired by consumers. For production of seedless watermelon, optimum pollination characteristics of the pollinating plant are desired.

Seedless watermelon plants are triploid and must be pollinated by the pollen of diploid watermelon plants. To provide adequate pollination of seedless watermelon plants, it is current practice to plant diploid pollenizer plants over approximately 25-33% of the field surface. The remaining portion of the field is planted with the triploid plants. Thus, to maximize the value of the crop in the field, growers use high yield marketable diploid watermelon varieties, which ultimately compete with the triploid seedless varieties for sun, nutrients, and space.

A pollenizer for seedless watermelon producing small and unmarketable fruits, which are not harvested, has been disclosed (WO00/70933). However, when this pollenizer is used, a lower total yield of marketable fruit is observed when compared to a commercial pollenizer line. Also, the fruits of the pollenizer described in WO00/70933 that are not harvested become hosts for diseases in the future, and their seeds will germinate and grow into weeds, thus reducing future yields.

The present invention recognizes the need to increase the yield of the seedless watermelon, preferably without loss in total yields of marketable fruits. The present invention also recognizes that novel phenotypic characteristics of the diploid pollenizer plants are needed to permit these diploids to be planted in close proximity to the triploid plants and to share the field surface with the triploid plants, thereby effectively decreasing the surface area of the field required for the diploid pollenizers of the invention. The present invention also recognizes the need to minimize the carryover of un-harvested pollenizer fruits as weeds into the subsequent season. The present invention also recognizes the need to increase the pollinating capacity of diploid watermelon plants in order to further decrease the ratio of diploid to triploid plants in the field, thereby also increasing the yield of the seedless watermelon. The present invention also further recognizes the needs to allow farmers to distinguish the seedless fruits from the fruits of the pollenizer in the field and to provide marketable value to the pollenizer fruits themselves.

SUMMARY OF THE INVENTION

The present invention uses a novel diploid watermelon to improve current methods of commercial production of seedless watermelon and to increase seedless watermelon yield. According to the invention, there is provided a novel enhanced, pollenizer diploid watermelon (hereinafter referred to as "enhanced pollenizer") and method for pollinating seedless watermelon plants. The present invention includes an enhanced pollenizer comprising, at maturity, small leaves. The present invention further includes an enhanced pollenizer comprising, at maturity, brittle fruits. The present invention includes an enhanced pollenizer comprising, at maturity, small leaves and bearing brittle fruits. The small leaves allow the enhanced pollenizer to be grown in close proximity to the triploid watermelon plants without competing with them, thereby increasing yields of seedless fruits. The brittleness of the fruit offers the advantage that un-harvested fruits of the pollenizer can be easily destroyed through conventional field preparation for minimizing carry over as weeds in future plantings.

In one embodiment, the enhanced pollenizer of the present invention further comprises heavily branching lacy vines (also referred to as heavily branched open vines) and therefore preferably comprises a high number of open (lacy) branches. The heavily branching vines allow an enhanced pollenizer of this invention to produce very large amount of male flowers to pollinate the female flowers of the triploid plant, to produce the seedless fruit. In one embodiment, the leaves of the enhanced pollenizer also comprise non-overlapping, deep lobes. The openness of the branched or lacy vine results, in part, from the distinct small and non-overlapping, deep lobed leaves. The lacy branches and the small leaves, in one embodiment with non-overlapping, deep lobes, of the invention have the additional advantage to provide more access of bees to the flowers of both the pollenizing and the triploid plant, thereby enhancing transfer of the pollen from enhanced pollenizer watermelon to the female flowers of the triploid watermelon. Easier access by bees to the male flowers of the enhanced pollenizer and coupled with a greater frequency of male flowers provides a greater pollen source for triploid fruit production.

A second advantage of small leaves, in one embodiment characterized by deep, non-overlapping lobes, is that more sunlight is able to penetrate to adjacent triploid plants. A third advantage of small leaves, in one embodiment characterized by deep, non-overlapping lobes, is that these leaves take up less field area than the substantially larger leaves of the diploid pollenizers currently used in the production of seedless watermelon. Thus, as it is less competitive for light, water and fertilizers, the enhanced pollenizer of the present invention can also be grown closer to the triploid plants, and it does not need dedicated space to grow. In one embodiment, when the enhanced pollenizer and method of the present invention are used, the triploid seedless watermelon are grown in solid rows at a standard spacing, the enhanced pollenizer being then inter-planted between the plants within the rows. This results in significantly higher numbers of triploid plants per acre compared to the number of triploid watermelon plants that has traditionally been planted, and higher yields of seedless fruits.

In one embodiment, the fruit of the enhanced pollenizer of the present invention are small and therefore easier to distinguish from the seedless fruits in the field. Therefore, also according to the present invention, there is provided a novel enhanced pollenizer comprising small fruits with brittle rind. The small fruits with brittle rind also reduce the load to the plant and allow the plant to continue flowering for extended periods of time, significantly greater than pollenizer watermelons that are currently used in the production of seedless watermelon. The longer flowering duration of the enhanced pollenizer, compared to traditional pollenizer diploid watermelons, results in increased fruit set and yield of seedless watermelon. The brittle rind also offers the advantage that un-harvested fruits of the pollenizer quickly decompose in the fields, and can be easily eliminated from further re-production through conventional crop disposal (discing and plowing). The brittle rind also offers the advantage of differentiating the fruit of pollenizer from the fruit of triploid seedless watermelon, even when they are similar in appearance.

An additional advantage of the enhanced pollenizer of the present invention is also that its fruits contain very large amounts of seeds, which can be harvested and sold as edible watermelon seeds for food or feed uses, or for use in medicines. This provides additional value to the grower who can harvest and market the fruits of the enhanced pollenizer as such or its seeds.

The present invention also includes an enhanced pollenizer fruit that weighs approximately in the range of about 2 to 7 lbs, in one embodiment about 2 to about 6 lbs, in one embodiment about 2 to about 5 lbs. In one embodiment, the average weight for the fruits of the enhanced pollenizer is about 3.2 lbs.

In one embodiment, the present invention further includes an enhanced pollenizer fruit rind that is brittle, breaking under a pressure approximately in the range of about 7 to about 11 lbs/in$^2$. In another embodiment, an enhanced pollenizer fruit rind breaks under a pressure approximately in the range of about 90 to about 150 g/mm$^2$, in one embodiment about 100 to about 148 g/mm$^2$, in one embodiment about 110 to about 145 g/mm$^2$, in one embodiment about 120 to about 140 g/mm$^2$.

In one embodiment, the rind of a fruit an enhanced pollenizer of the instant invention breaks under a pressure of not more than about 1,800 g when a fruit tester with a 2 mm tip is used. In one embodiment, the fruit rind of an enhanced pollenizer of the instant invention breaks under a pressure approximately in the range of about 400 g to about 1,800 g when a fruit tester with a 2 mm tip is used.

In one embodiment, the fruit rind of an enhanced pollenizer of the instant invention breaks under a pressure of not more than about 2,300 g when a fruit tester with a 3 mm tip is used. In one embodiment, the fruit rind of an enhanced pollenizer of the instant invention breaks under a pressure approximately in the range of about 1,000 g to about 2,300 g when a fruit tester with a 3 mm tip is used.

In one embodiment, the average pressure to break the rind of a fruit of an enhanced pollenizer of the present invention is not more than about 1,300 g when a fruit tester with a 2 mm tip is used. In one embodiment, the average pressure to break the rind of a fruit of an enhanced pollenizer of the present invention is approximately in the range of about 700 g to about 1,300 g when a fruit tester with a 2 mm tip is used.

In one embodiment, the average pressure to break the rind of a fruit of an enhanced pollenizer of the present invention is not more than about 2,000 g when a fruit tester with a 3 mm tip is used. In one embodiment, the average pressure to break the rind of a fruit of an enhanced pollenizer of the present invention is approximately in the range of about 1,400 g to about 2,000 g when a fruit tester with a 3 mm tip is used.

In one embodiment, the present invention includes an enhanced pollenizer having leaves with a surface area approximately in the range of about 20 to about 70 cm$^2$, in one embodiment about 22.5 to about 50 cm$^2$, in one embodiment about 25 to about 40 cm$^2$. In one embodiment, the average leaf surface area of leaves of the enhanced pollenizer is approximately about 25 to about 40 cm$^2$, in one embodiment about 27.5 to about 37.5 cm$^2$, in one embodiment about 30 to about 35 cm$^2$.

In one embodiment, the surface area of the 5$^{th}$ leaf on a vine of an enhanced pollenizer of the present invention counted from the smallest new leaf at the tip of the vine towards the crown of the plant is not more than about 50 cm$^2$. In one embodiment, the surface area of such 5$^{th}$ leaf from the smallest new leaf on a vine of an enhanced pollenizer of the instant invention is approximately in the range of about 15 cm$^2$ to about 50 cm$^2$. In one embodiment, the average leaf surface area of such 5$^{th}$ leaves from the smallest new leaf on a vine of an enhanced pollenizer of the instant invention is not more than about 40 cm$^2$. In one embodiment, the average leaf surface area of the 5$^{th}$ leaves from the smallest new leaf on a vine of an enhanced pollenizer is approximately in the range of about 20 cm$^2$ to about 40 cm$^2$.

Also included in the invention is an enhanced pollenizer plant for pollinating triploid plants producing seedless watermelon fruit, comprising, at maturity, the characteristics of smaller leaf size compared to the watermelon variety SANGRIA™, wherein the fruit rind is more brittle than the rind of the variety SANGRIA™ (a commercial variety of Syngenta Seeds, Inc.). In one embodiment, the average leaf surface area of leaves of an enhanced pollenizer of the present invention is about 3 to about 14 times smaller than that of watermelon variety SANGRIA™. In one embodiment, the fruit rind of an enhanced pollenizer of the present invention is about 2 to about 4 times more brittle than the fruit rind of watermelon variety SANGRIA™. In one embodiment, the enhanced pollenizer further comprises small fruits. In one embodiment, the leaves of the enhanced pollenizer comprise deep, non-overlapping lobes.

The pollenizer diploid watermelon of the invention is further enhanced by including resistance to various pests and herbicides via conventional plant breeding methods or genetic transformation.

The present invention also provides a method for inter-planting enhanced pollenizer plants amongst the triploid watermelon plants in a field in a pattern that decreases the ratio of pollenizer plants to triploid plants and increases the field surface for triploid plants. This allows for a higher population of triploid plants, than conventional practices, and results in 25-33% higher yield of seedless fruits.

Also included in the present invention is a method of increasing the yield of triploid, seedless watermelon comprising the steps of reducing fruit load of said enhanced pollenizer watermelon, increasing the flowering duration of said pollenizer watermelon, planting said enhanced pollenizer watermelon in a field of triploid watermelon; and harvesting said triploid watermelon.

The invention also provides a method of increasing the yield of triploid seedless watermelon plants by using enhanced pollenizer watermelon plants, in one embodiment with small fruits, wherein the fruit as such are not harvested for human consumption. In one embodiment, the seeds of the fruits of the enhanced pollenizer are used as food or feed, or in medicines.

The present invention also provides a method for producing an enhanced pollenizer according to the present invention comprising crossing a first watermelon plant having small leaves with a second watermelon plant producing fruit with brittle rind that splits easily and selecting for a watermelon plant having the characteristics of the enhanced pollenizer disclosed herein. In one embodiment, the first watermelon plant further comprises the characteristic of a heavily branching lacy vine. In one embodiment, the leaves of the enhanced pollenizer comprises deep, non-overlapping lobes. In one embodiment, the first watermelon plant has the characteristics of OW824 disclosed herein. In one embodiment, the second watermelon plant bears small fruit. In one embodiment, the second watermelon plant has the characteristics of OW823 disclosed herein. In one embodiment, the first watermelon plant is OW824. In one embodiment, the second watermelon plant is OW823. In another embodiment, the first watermelon plant is OW824 and the second watermelon plant is OW823. In one embodiment, the method further comprises fixing the traits of the enhanced pollenizer.

The present invention also discloses a watermelon enhanced pollenizer obtainable by a method comprising the steps of a) crossing a watermelon plant with a plant of NO1F3203B (now called SP-1) deposited under Accession No. PTA-4856, b) obtaining a progeny, c) selecting said progeny for the characteristics of the enhanced pollenizer, preferably small leaves and brittle fruit, In one embodiment, it is further selected for heavily branching lacy vines, in one embodiment for small fruit. In one embodiment, the method further comprises crossing said progeny either with itself or with a plant of NO1F3203B, or with another enhanced pollenizer, and selecting for the said characteristics of the enhanced pollenizer. In one embodiment, the method further comprises fixing the traits of the enhanced pollenizer.

In one embodiment, an enhanced pollenizer of the instant invention is an inbred or a hybrid. In one embodiment, an enhanced pollenizer of the instant invention is a dihaploid.

In one embodiment, the present invention discloses a method of producing seeds of an enhanced pollenizer comprising: a) growing a plant of an enhanced pollenizer according to the present invention; b) allowing self-pollination of said plant; c) harvesting seeds from said plant. In one embodiment, the method further comprises washing and drying said seed.

In one embodiment, the present invention discloses a method of vegetative propagating an enhanced pollenizer of the present invention comprising: a) collecting shoot tissue of a plant of an enhanced pollenizer; b) cultivating said tissue to obtain proliferated shoots; c) rooting said proliferated shoots to obtain rooted plantlets. In one embodiment, the method further comprises growing plants from said rooted plantlets. In one embodiment, the method further comprises harvesting seeds from said plants. In one embodiment, the method further comprises washing and drying said seed.

In one embodiment, the present invention discloses a method for producing triploid, seedless watermelon fruit comprising the steps of: a) inter-planting a seed or a plant of an enhanced pollenizer according to the present invention and seed or plants of triploid watermelon plants in a field; and b) allowing pollination of said triploid watermelon plants by pollen of said diploid watermelon plant to obtain triploid, seedless watermelon fruit. In one embodiment, the method further comprises harvesting seeds from said plants. In one embodiment, the method further comprises washing and drying said seed.

DETAILED DESCRIPTION OF THE INVENTION

Development of Seedless Watermelons

Triploid watermelons are created by crossing a tetraploid (4X) female parent line with diploid (2X) male parent line. The resulting triploid (3X) watermelon seeds or plants are planted in a field with diploid watermelon pollenizers. The resulting fruit of the triploid watermelon are seedless.

To create a tetraploid female watermelon line, it is known in the art to use chemicals that alter mitosis of a diploid inbred line so that unusual numbers of chromosomes are obtained. For example, colchicine is a chemical that alters the mitotic spindle fibers of diploid cells resulting in a number of cells that are tetraploid. The diploid line used to create a tetraploid is selected based on the traits desired for the tetraploid line. Traits that are desired for a tetraploid line may therefore first be introgressed into the diploid inbred lines that will be used to develop the tetraploid lines by breeding methods well known to those skilled in the art. Thus, the diploid and tetraploid parent lines are bred separately for the desired traits.

It usually requires at least two generations of self-pollination and selection to "fix" the 4X condition, after the colchicine treatment generation because, often, chromosomal aberrations are encountered that affect seed fertility, and must be eliminated. Once the stable tetraploid containing the desired characteristics is verified, it then can be used as a stable female parent for the production of the triploid hybrid. A stable diploid inbred is selected for use as the male parent. Methods for developing tetraploid plants are described in Kihara, H., 1951, Triploid Watermelons, *Proceedings of American Society for Horticultural Science* 58:217-230; and Eigsti, O. J., 1971, Seedless Triploids, HortScience 6, pgs. 1-2.

The tetraploid female parent line and diploid male parent line are planted in a seed production field. The pollen of the diploid male parent is transferred to the female tetraploid flower by methods well known to those skilled in the art. The triploid seed that is produced is present in the resulting fruit and is planted to produce the triploid plants. The breeding of watermelon is further described in Mark Bassett (Editor), 1986, Breeding Vegetable Crops, AVI Publishing, ISBN 0-87055-499-9.

A triploid seedless watermelon is a true F1 hybrid between a tetraploid watermelon, as the female parent, and a diploid watermelon, as the male parent (Kihara, H. 1951. Triploid Watermelons. *Proceedings of American Society for Horticultural Science* 58:217-230). The seedless condition in triploid watermelon is the result of the presence of three homologous sets of chromosomes per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Adequate viable pollen supply from the diploid pollenizer watermelon is essential for the triploid female flowers to set and develop into regular seedless fruit. The female flowers of triploid watermelon will not set if they are not pollinated by viable pollen of diploid watermelon. (Maynard, D. N. (editor), 2001, *Watermelons: Characteristics, Production and Marketing*, ASHS Press, ISBN 0-9707546-1-2). The diploid watermelon grown in a field of triploid plants is referred to herein as the "pollenizer." In current commercial triploid watermelon production fields, the triploid watermelon and diploid pollenizer are inter-planted, either within row or between rows, in a ratio of approximately 1 diploid to 2 or 3 triploids. Although research has indicated a 1:4 ratio is acceptable, it is rarely used in commercial plots. (NeSmith, D. S., Duval, J. R. *Fruit Set of Triploid Watermelons as a Function of Distance from a Diploid Pollenizer*, HortScience 36(1): 60-61, 2001)

Development of Enhanced Pollenizer Diploid Watermelon

According to the present invention, a watermelon (OW824) is selected having the characteristics of a heavily branching lacy vine, early and prolific male flowers, and small leaves with deep, non-overlapping leaf lobes. In this example, the fruit of OW824 is relatively large, the rind and flesh are very firm, the seed size is very big and the flesh is white. OW824 is a publicly available edible seed watermelon variety generally referred to as XinJiang edible seed watermelon.

Also according to the invention, a hybrid watermelon (OW823) is selected for its small fruit (2-3 kg) with brittle rind that splits easily. OW823 also includes the characteristics of mid-sized seeds with yellow flesh and has relatively large leaves. OW823 is a commercially available variety, Tiny Orchid, from Known-You Seeds, Ltd. of Taiwan.

Crossing OW824×OW823 generated progeny having the characteristics of the enhanced pollenizer diploid watermelon of the present invention as described in more detail below.

The initial cross of OW824×OW823 was made during the summer of 2000 in California. The $F_1$ generation was grown in the greenhouse in the fall of 2000. The $F_2$ population was grown Florida in the spring, and in California in the summer of 2001. Individuals with the set of traits required for the enhanced pollenizer were successfully identified and self-pollinated in $F_2$ populations grown in both locations. A total 7 selections were made. The 7 $F_3$ lines were grown in the field in Florida and the greenhouse in California in the fall of 2001 for further selection and evaluation. Three $F_3$ lines were identified to best meet our breeding goals and advanced to $F_4$ generation. They all have the set of the traits required by the enhanced pollenizer. One line, NO1F3203B, now called SP-1, is fixed for every trait concerned. NO1F3203B contains the traits that are illustrative of the traits of the enhanced pollenizer of the invention. Other enhanced pollenizer lines with similar characteristics were for example SP-2 with slightly larger leaves than SP-1, and SP-3 with slightly larger fruits than SP-1 and a different fruit skin color.

Leaf: The leaves of the enhanced pollenizer are significantly smaller and are more numerous than that of the commonly used pollenizers such as the variety SANGRIA™ (See FIGS. 1 and 2). The size of a leaf is determined by measuring its surface area. The surface area of different types of leaves of a watermelon plant can be measured. In one embodiment, the surface area of the $5^{th}$ leaf on a vine, counted from the smallest new leaf at the tip of the vine towards the crown of the plant, is measured. The smallest new leaf at the tip of a vine is typically about 5 cm in length and width, and is counted as the first leaf. Such $5^{th}$ leaf is generally referred to herein as the $5^{th}$ leaf from the smallest new leaf on a vine. In another embodiment, the surface area of an average mature and fully developed leaf is measured. An average mature and fully developed leave is for example a leaf at the fifth node from the crown of a plant. In another embodiment, the surface area of the leaves, which appear to be the largest on a plant, is measured.

In one embodiment, the leaves of an enhanced pollenizer of the present invention have a surface area approximately in the range of about 20 to about 70 $cm^2$, in one embodiment about 22.5 to about 50 $cm^2$, in one embodiment about 25 to about 40 $cm^2$. In another embodiment, the average leaf surface area of the leaves of the enhanced pollenizer is approximately about 25 to about 40 $cm^2$, in one embodiment about 27.5 to about 37.5 $cm^2$, in one embodiment about 30 to about 35 $cm^2$.

In one embodiment, the surface area of the $5^{th}$ leaf from the smallest new leaf on a vine of an enhanced pollenizer of the present invention is measured. In one embodiment, the surface area of the $5^{th}$ leaf from the smallest new leaf on a vine of an enhanced pollenizer of the present invention is not more than about 50 $cm^2$. In one embodiment, the surface area of the $5^{th}$ leaf from the smallest new leaf on a vine of an enhanced pollenizer of the instant invention is approximately in the range of about 15 $cm^2$ to about 50 $cm^2$. In one embodiment, the average leaf surface area of $5^{th}$ leaves from the smallest new leaf on a vine of an enhanced pollenizer of the present invention is not more than about 40 $cm^2$. In one embodiment, the average leaf surface area of $5^{th}$ leaves from the smallest new leaf on a vine of an enhanced pollenizer of the present invention is approximately in the range of about 20 to about 40 $cm^2$. For example, Tables 1A and 1D below describe measurements of the surface area of $5^{th}$ leaves from the smallest new leaf on a vine of NO1F3203B/SP-1.

In one embodiment, the surface area of average mature and fully developed leaves of an enhanced pollenizer of the present invention is measured. In one embodiment, the surface area of such average mature and fully developed leaves of an enhanced pollenizer of the present invention is not more about 90 $cm^2$. In one embodiment, the surface area of an average mature and fully developed leaf of an enhanced pollenizer of the present invention is approximately in the range of about 40 $cm^2$ to about 90 $cm^2$. For example, Tables 1C and 1D below describe measurements of the surface area of average mature and fully developed leaves of NO1F3203B/SP-1.

In one embodiment, the surface area of largest leaves of plants of the enhanced pollenizer of the present invention is determined. In one embodiment, such largest leaves have a surface area not more than about 120 cm², in one embodiment approximately in the range of about 60 cm² to about 120 cm². For example, Table 1B below describes measurements of the surface area of such large leaves of NO1F3203B/SP-1.

Clearly, due to various environmental and physiological conditions, the size of the leaves of a watermelon plant may vary. Accordingly, in one embodiment, at least about 80% of the leaves of an enhanced pollenizer of the instant invention in a field show the above characteristics of surface area. In one embodiment, at least about 90% of the leaves of an enhanced pollenizer of the instant invention in a field show the above characteristics of surface area.

In one embodiment, the leaves of the enhanced pollenizer have deep, non-overlapping leaf lobes.

The leaf surface areas of the enhanced pollenizer NO1F3203B and the SANGRIA™, a pollenizer favoured by growers, are shown for comparison purposes in Table 1 A-1D.

In Table 1A the leaves for both NO1F3203B and SANGRIA™ were taken from mature plants sowed on Aug. 20, 2001 and harvested on Nov. 8, 2001. In Table A, 5$^{th}$ leaves from the smallest new leaf on a vine were harvested.

In Table 1B the leaves of both NO1F3203B and SANGRIA™ were taken from mature plants sowed on Aug. 7, 2003, transplanted to open fields on Sep. 9, 2003 and harvested on Oct. 31, 2003. In Table 1B, leaves, which appeared to be the largest leaves on the plants, were harvested.

In Table 1C leaves of both NO1F3203B and SANGRIA™ were taken from mature plants sowed on Aug. 7, 2003, transplanted to open fields on Sep. 9, 2003 and harvested on Dec. 4, 2003. The leaves used in Table 1C were average mature and fully expanded leaves at the fifth node from the crown of the plant.

In Table 1D the leaves for both NO1F3203B and SANGRIA™ were taken from mature plants sowed on Jan. 16, 2004 and harvested on May 16, 2004. Average mature and fully developed leaves (M) and 5$^{th}$ leaves from the smallest new leaf on a vine (Y) were harvested. The data in the Tables are given in cm² (also given in square inches (sq. in.) in Table 1B and 1C).

Plants were grown at the Naples station in Florida. Leaf samples were collected and the leaves photocopied. In Table 1A, the surface area of the leaves was determined using graph paper. In Tables 1B-D, the photocopies of leaves were scanned and the surface area determined using a computer. In particular, in Table 1D, a WinRhizo STD 1600+scanner and the program WinRhizo Pro 2003 were used to analyze the leaf images.

TABLE 1A

| NO1F3203B LEAF | cm² | SANGRIA LEAF | cm² |
|---|---|---|---|
| A | 38.75 | A | 232.00 |
| B | 26.25 | B | 447.25 |
| C | 39.75 | C | 241.50 |
| D | 28.75 | D | 238.00 |
| E | 38.25 | E | 211.00 |
| F | 26.27 | | |
| Average (±Std Dev) | 33.08 (±6.46) | | 273.95 (±97.60) |

TABLE 1B

| Sample | NO1F3203B cm² (sq. in.) | SANGRIA ™ cm² (sq. in.) |
|---|---|---|
| 1 | 63.42 (9.83) | 301.81 (46.78) |
| 2 | 100.19 (15.53) | 285.81 (44.30) |
| 3 | 103.87 (16.10) | 212.00 (32.86) |
| 4 | 78.00 (12.09) | 334.77 (51.89) |
| 5 | 114.58 (17.76) | 330.90 (51.29) |
| Average | 92.00 (14.26) | 293.03 (45.42) |
| Std Dev | 20.77 (3.22) | 49.67 (7.70) |

TABLE 1C

| Sample | NO1F3203B LEAF cm² (sq. in.) | SANGRIA LEAF cm² (sq. in.) |
|---|---|---|
| 1 | 59.16 (9.17) | 213.03 (33.02) |
| 2 | 51.35 (7.96) | 242.37 (37.57) |
| 3 | 51.48 (7.98) | 265.10 (41.09) |
| 4 | 43.74 (6.78) | 245.16 (38.00) |
| 5 | 57.94 (8.98) | 274.25 (42.51) |
| Average | 52.71 (8.17) | 248.00 (38.44) |
| Sdt Dev | 5.53 (0.86) | 21.19 (3.28) |

TABLE 1D

| | Leaf Stage | Leaf ID | Area (cm2) | Average | Std Dev |
|---|---|---|---|---|---|
| SP-1 | Y | sp6-1 | 18.79 | | |
| SP-1 | Y | sp6-2 | 40.31 | | |
| SP-1 | Y | sp6-3 | 19.00 | | |
| SP-1 | Y | sp6-4 | 32.34 | | |
| SP-1 | Y | sp6-5 | 22.47 | 26.58 | 7.79 |
| SANGRIA ™ | Y | sg6-1 | 120.35 | | |
| SANGRIA ™ | Y | sg6-2 | 119.00 | | |
| SANGRIA ™ | Y | sg6-3 | 103.16 | | |
| SANGRIA ™ | Y | sg6-4 | 152.82 | | |
| SANGRIA ™ | Y | sg6-5 | 118.09 | 122.68 | 12.06 |
| SP-1 | M | sp-1 | 60.99 | | |
| SP-1 | M | sp-2 | 59.01 | | |
| SP-1 | M | sp-3 | 44.05 | | |
| SP-1 | M | sp-4 | 80.91 | | |
| SP-1 | M | sp-5 | 81.56 | | |
| SP-1 | M | sp-6 | 64.49 | | |
| SP-1 | M | sp-7 | 60.61 | | |
| SP-1 | M | sp-8 | 51.06 | | |
| SP-1 | M | sp-9 | 51.88 | | |
| SP-1 | M | sp-10 | 41.55 | 59.61 | 10.10 |
| SANGRIA ™ | M | sg-1 | 218.92 | | |
| SANGRIA ™ | M | sg-2 | 317.81 | | |
| SANGRIA ™ | M | sg-3 | 261.77 | | |
| SANGRIA ™ | M | sg-4 | 244.82 | | |
| SANGRIA ™ | M | sg-5 | 235.53 | | |
| SANGRIA ™ | M | sg-6 | 234.35 | | |
| SANGRIA ™ | M | sg-7 | 255.25 | | |
| SANGRIA ™ | M | sg-8 | 261.73 | | |
| SANGRIA ™ | M | sg-9 | 237.72 | | |
| SANGRIA ™ | M | sg-10 | 240.58 | 250.85 | 18.63 |

In one embodiment, the surface area of the enhanced pollenizer leaf of the invention is approximately 3 to 14 times less than the surface area of the typical diploid pollenizer, SANGRIA™ plant. In one embodiment, the surface area of the enhanced pollenizer leaf of the invention is approximately 5 to 12 times less than the surface area of the typical diploid pollenizer, SANGRIA™ plant.

Figure 1:
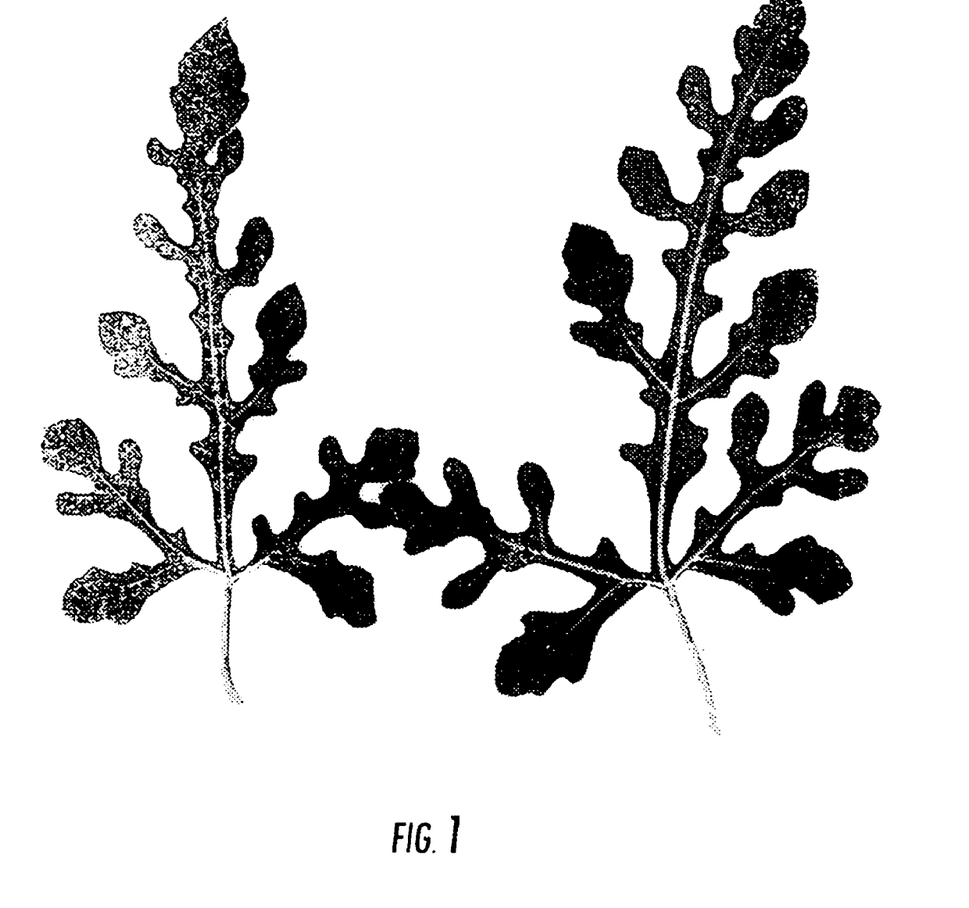
FIG. 1 is a photographic depiction of a leaf of the enhanced pollenizer plant of the invention.
Figure 2:
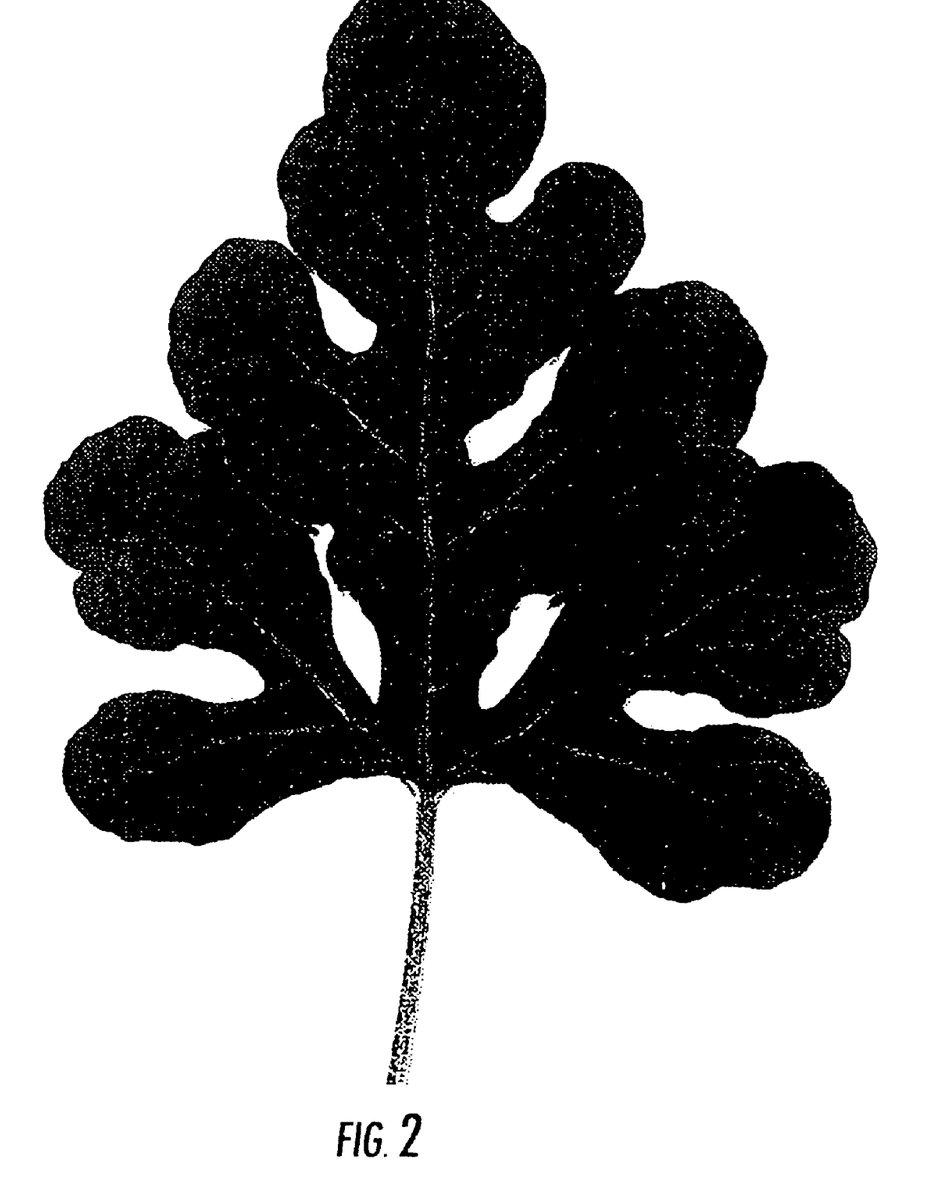
FIG. 2 is a photographic depiction of a leaf of the pollenizer referred to as SANGRIA™ that is currently used in commerce.

FIG. 1 illustrates the non-overlapping characteristic of the deep, non-overlapping lobed leaves of the enhanced pollenizer. Clearly, due to various environmental and physical forces, some of the leaves in this population may have some overlapping lobes, but overlapping lobes are not characteristic thereof. In contrast, the SANGRIA™ leaf shown in FIG. 2 is characterized as having leaf lobes that habitually overlap each other. The small, deeply lobed and non-overlapping leaves of the invention allow more sunlight through to adjacent triploid watermelon plants.

Branching: In one embodiment, an enhanced pollenizer of the invention is also heavily branched (also referred to as "lacy vines" or "open vines"), having significantly more branches (average of 25.9) than the variety referred to as SANGRIA™, (average of 13). In one embodiment, an enhanced pollenizer of the present invention produces secondary and tertiary branches on the main branch, thus allowing for very large amounts of male flowers. Moreover, in one embodiment, an enhanced pollenizer of the present invention, for example, a plant of SP-1, also develops tertiary branches late in the season, a characteristic rarely observed on regular watermelon plant like SANGRIA™. The lacy vine characteristic enables the enhanced pollenizer to produce more accessible male flowers than current diploid pollenizers, thereby enhancing exposure of the flowers to bees. The open or lacy vines also permit the interplanting of the enhanced pollenizer between triploid plants thereby allowing for higher triploid populations and greater seedless fruit production.

Fruit: The fruit rind of the enhanced pollenizer is very brittle and is easily broken. The brittle fruit rind splits easily, due to natural maturation or by breaking or splitting of the fruit during harvest of the seedless triploid watermelon (for example from foot traffic). Splitting of fruit signals the plant that it hasn't completed its reproductive process inducing the plant to continue flowering for a longer period of time. Brittleness is conferred by a gene e (explosive rind, thin, and tender rind, bursting when cut (Rhodes & Dane, 1999, *Gene List for Watermelon*, Cucurbit Genetics Cooperative Report 22:71-77; Nihat Guner & Todd C. Wehner, 2003, *Gene List for Watermelon*, Cucurbit Genetics Cooperative Report 26:76-92; Porter D. R. (1937) Inheritance of certain fruit and see characters in watermelon Hilgardia 10: 489-509; Poole C. F. (1944) Genetics of cultivated cucurbits J. Hered. 35: 122-128). Accordingly, in one embodiment, the brittleness of the fruit of an enhanced pollenizer of the present invention is conferred by a gene e, and the present invention includes the use of a watermelon plant comprising a gene e as pollenizer for triploid watermelon plants.

When measured by a penetrometer, a fruit of NO1F3203B breaks at about 7-11 lbs/in$^2$, whereas a fruit of a typical watermelon such as SANGRIA™ breaks at about 21-27 lbs/in$^2$. Accordingly, in one embodiment, the fruit rind of an enhanced pollenizer of the present invention is about 2 to about 4 times more brittle than the fruit rind of watermelon variety SANGRIA™. In one embodiment, using a Tester FT02 of Wagner Instruments, Greenwich, Conn. 06836, the fruit of the enhanced pollenizer breaks under a pressure approximately in the range of about 90 to about 150 g/mm$^2$, in one embodiment about 100 to about 148 g/mm$^2$, in one embodiment about 110 to about 145 g/mm$^2$, in one embodiment about 120 to about 140 g/mm$^2$. By comparison, the fruit of SANGRIA™ breaks under a pressure of approximately about 300 g/mm$^2$.

In one embodiment, measurements of the brittleness of a watermelon fruit are carried out with a Tester FT327, a Tester FT011 or a Tester FT02 from Wagner Instruments, Greenwich, Conn. 06836, with a 2 mm or a 3 mm tip.

In one embodiment, the rind of a fruit of an enhanced an enhanced pollenizer of the instant invention breaks under a pressure under about 1,800 g when a fruit tester with a 2 mm tip is used. In one embodiment, the fruit rind of an enhanced an enhanced pollenizer of the instant invention breaks under a pressure approximately in the range of about 400 g to about 1,800 g when a fruit tester with a 2 mm tip is used.

In one embodiment, the fruit rind of an enhanced an enhanced pollenizer of the instant invention breaks under a pressure under about 2,300 g when a fruit tester with a 3 mm tip is used. In one embodiment, the fruit rind of an enhanced an enhanced pollenizer of the instant invention breaks under a pressure approximately in the range of about 1,000 g to about 2,300 g when a fruit tester with a 3 mm tip is used.

In one embodiment, the average pressure to break the rind of a fruit of an enhanced pollenizer of the present invention is under about 1,300 g when a fruit tester with a 2 mm tip is used. In one embodiment, the average pressure to break the rind of a fruit of an enhanced pollenizer of the present invention is approximately in the range of about 700 g to about 1,300 g when a fruit tester with a 2 mm tip is used.

In one embodiment, the average pressure to break the rind of a fruit of an enhanced pollenizer of the present invention is under about 2,000 g when a fruit tester with a 3 mm tip is used. In one embodiment, the average pressure to break the rind of a fruit of an enhanced pollenizer of the present invention is approximately in the range of about 1,400 g to about 2,000 g when a fruit tester with a 3 mm tip is used.

In one embodiment, at least about 80% of the fruits of a plant of the instant invention in a field show the above characteristics of rind brittleness. In one embodiment, at least about 90% of the fruits of a plant of the instant invention in a field show the above characteristics of rind brittleness.

The environmental conditions generally influence the brittleness of the rind of a fruit of the present invention. For example, the rind of fruits grown under warm and sunny conditions tends to be more brittle than that of fruits grown under cooler and shadier conditions. This is for example reflected in the measurements of Example 12, where a Spring crop was tested compared to a Fall crop in Examples 10 and 11.

In one embodiment, the fruit size of the enhanced pollenizer is approximately in the range of about 5 to about 7 inches long×about 6 to about 8 inches wide. In one embodiment, the fruit size of the enhanced pollenizer is approximately about 6 inches long×about 7 inches wide, whereas the typical pollenizer is about 10 inches long×20 inches wide. Small fruit size, as well its brittleness was selected to decrease the load on the plant, thereby extending the duration of plant growth and flower production. Another advantage of the small fruit size is that it enables the harvester to easily distinguish the seedless fruit from seeded fruit, is often difficult with currently used pollenizers, which are selected based on their overall similarity to the seedless triploid plants. The fruit of the enhanced pollenizer weighs approximately in the range of about 2 to about 7 lbs, in one embodiment about 2 to about 6 lbs, in one embodiment about 2 to about 5 lbs. In one embodiment, the average weight for the fruits of the enhanced pollenizer is about 3.2 lbs.

In one embodiment, the rind color of the enhanced pollenizer is light green with very thin dark green lines. The fruit of the enhanced pollenizer of the invention can be distinguished from the fruit of most (about 99%) of the commercially available seedless watermelon varieties.

Flowering: The plants of the enhanced pollenizer, e.g. of NO1F3203B, also flower approximately 7 to 10 days earlier than diploid pollenizer plants currently used for the production of seedless watermelon, and continue flowering during fruit harvest time of the seedless watermelon, 2 to 3 weeks longer than standard diploid pollenizer plants. Thus, the pollenizer plant of the invention has a flowering duration that is approximately 3 to 5 weeks longer than pollenizers currently used.

Other Traits: The enhanced pollenizer, e.g. NO1F3203B, can be used either as donor of the set of traits disclosed above, or as the recurrent parent to develop additional enhanced pollenizer lines. In accordance with the invention, the enhanced pollenizer watermelon contains traits of disease resistance (e.g. Fusarium wilt, Anthracnose, Gummy Stem Blight, Powdery Mildew, and Bacterial Fruit Blotch), insect resistance (e.g. cucumber beetle, aphids, white flies and mites), salt tolerance, cold tolerance and/or herbicide resistance added. These traits can be added to existing lines by using either conventional backcrossing method, pedigree breeding method or genetic transformation. The methods of conventional watermelon breeding are taught in several reference books, e.g. Maynard, D. N. (editor), 2001, WATERMELONS Characteristics, Production and Marketing, ASHS Press; Mohr, H. C., Watermelon Breeding, in Mark J. Bassett (editor), 1986, Breeding Vegetable Crops, AVI Publishing Company, Inc. General methods of genetic transformation can be learned from publish references, e.g. Glich et al., (Eds), 1993, Methods in Plant Molecular Biology & Biotechnology, CRC Press, and more specifically for watermelon in WO02/14523.

Forms of the Enhanced Diploid Pollenizer: Once the enhanced pollenizer lines are developed, several forms of enhanced pollenizer varieties can be used in commercial seedless watermelon production. Specifically, these forms of enhanced pollenizer varieties include: Forms of Enhanced Pollenizer: (1) Open Pollinated Variety: The stable, enhanced lines of the enhanced pollenizer are grown in isolated fields, at least 2,000 meters from other watermelon varieties. Pollination is conducted in the open fields by bees. Seeds are harvested from the seed production field when the fruit and seeds are fully developed. The seeds are dried and processed according to the regular watermelon seed handling procedures. (2) Synthetic Variety: The seed of different enhanced pollenizer lines are individually produced in isolated fields. Bee pollination is used in each isolation. The seed of different enhanced pollenizer are separately harvested and processed. Mixing several enhanced pollenizer lines in various ratios forms the synthetic varieties. The synthetic variety can provide a broader pollenizer population for the triploid watermelons. (3) Open-Pollinated Hybrid Variety: Two or several enhanced pollenizer lines are planted in the same seed production field with bee pollination. The harvested seed lot, therefore, contains both hybrid and inbred seed. (4) Hybrid Variety: Two enhanced pollenizer lines, the male and female parents, are planted in the same field. Hand pollination is conducted. Only the seed from female parent line is harvested and sold to the commercial grower to use as pollenizer. Table 3 in Example 7 shows the results obtained using various combinations of inbred and hybrid enhanced pollenizers.

In one embodiment, an enhanced pollenizer of the present invention is a dihaploid. A dihaploid is for example produced by gamma-ray irradiation of the anthers followed by pollination of female flowers with irradiated pollen and embryo rescue. In one embodiment, an enhanced pollenizer is grafted on rootstock according to methods standard in the art.

Method of Seedless Watermelon Production: Most current commercial seedless watermelon growers in NAFTA use elongated diploid varieties with an Allsweet stripe pattern: light green skin with wide green stripes, as the pollenizer. The variety referred to as SANGRIA™ is the most preferred Allsweet type pollenizer and is available as a commercial product from Syngenta Seeds, Inc., Boise Id. Typically, the pollenizer is inter-planted with the triploid watermelon either between rows or within row. The current method of planting diploid pollenizers include planting the diploid plants at a distance from adjacent triploid such that they have the same field area available per plant as the field area that is available to the triploid watermelon plants. For example, currently watermelon growers inter-plant the diploids within a row, whereby the space between all adjacent plants within the row are approximately equidistant.

Alternatively, diploid pollenizer plants are planted in separate rows between rows of triploid watermelon plants. All rows of diploid and triploid plants in such a field are planted approximately equidistant from each other. In other words, under current methods for producing seedless watermelon, the width of all diploid and triploid rows is the same.

In one embodiment, a method of the present invention includes planting the enhanced pollenizer watermelon plants in rows that are narrower than the triploid rows, thereby saving field area for production of triploid seedless watermelon. In one embodiment, a method of the present invention includes planting an enhanced pollenizer watermelon plant within a row of triploid watermelon plants. In one embodiment, a method of the present invention includes planting an enhanced pollenizer watermelon plant and a triploid watermelon plant in the same hole. In one embodiment, enhanced pollenizer watermelon plants and triploid watermelon plants are planted in a ratio of 3-4:1, i.e. in every $3^{rd}$ or $4^{th}$ hole both an enhanced pollenizer plant and a triploid watermelon plant are planted in the same hole. In one embodiment, an enhanced pollenizer watermelon plant of the present invention is planted within pollinating distance of a triploid watermelon plant.

In one embodiment, a seed or a plant (e.g. a young plant about 2-4 weeks after sowing) of an enhanced pollenized of the present invention is planted in a field.

Table 2 below shows examples of different planting alternatives for watermelon pollenizer, including a preferred inter-planting according to the present invention (right column).

TABLE 2

| ○ | X | X | ○ | X | X | ○ | X | ○ | X | X | ○ | X | X | X | X | X | X | X | X |
|---|---|---|---|---|---|---|---|---|---|---|---|---|---|---|---|---|---|---|---|
|   |   |   |   |   |   |   |   |   |   |   |   |   |   | ♦ |   |   |   | ♦ |   |
| ○ | X | X | ○ | X | X | ○ | ○ | X | X | ○ | X | X | ○ | X | X | X | X | X | X |
|   |   |   |   |   |   |   |   |   |   |   |   | ♦ |   |   | ♦ |   |   |   | ♦ |
| ○ | X | X | ○ | X | X | ○ | X | X | ○ | X | X | ○ | X | X | X | X | X | X | X |
|   |   |   |   |   |   |   |   |   |   |   |   |   |   | ♦ |   |   | ♦ |   |   |
| ○ | X | X | ○ | X | X | ○ | X | ○ | X | X | ○ | X | X | X | X | X | X | X | X |
|   |   |   |   |   |   |   |   |   |   |   |   |   |   | ♦ |   |   |   | ♦ |   |
| ○ | X | X | ○ | X | X | ○ | ○ | X | X | ○ | X | X | ○ | X | X | X | X | X | X |
|   |   |   |   |   |   |   |   |   |   |   |   | ♦ |   |   | ♦ |   |   |   | ♦ |
| ○ | X | X | ○ | X | X | ○ | X | X | ○ | X | X | ○ | X | X | X | X | X | X | X |
|   |   |   |   |   |   |   |   |   |   |   |   |   |   | ♦ |   |   | ♦ |   |   |

TABLE 2-continued

| | | | | | | | | | | | | | | | | | | | | | | |
|---|---|---|---|---|---|---|---|---|---|---|---|---|---|---|---|---|---|---|---|---|---|---|
| ○ | X | X | ○ | X | X | ○ | | X | ○ | X | X | ○ | X | X | X | X | X | X | X | X | X |
| | | | | | | | | | | | | | | | | | ♦ | | | ♦ | | |
| ○ | X | X | ○ | X | X | ○ | | ○ | X | X | ○ | X | X | ○ | X | X | X | X | X | X | X |
| seeded | seedless | seedless | seeded | seedless | seedless | seeded | | Seeded = ○ Seedless = X | | | | | | | Pollenizer = ♦ Seedless = X | | | | | | |
| Conventional 2:1 pollenizer ratio using the row method | | | | | | | | Conventional 2:1 pollenizer ratio using the within row method | | | | | | | Pollenizer inter-planted at a 3:1 pollenizer ratio | | | | | | |

EXAMPLES

The following Examples are provided to illustrate the present invention, and should not be construed as limiting thereof.

Example 1

Triploid watermelon plants are planted in parallel rows 7 feet apart and 3 feet apart within each row. However, the enhanced diploid watermelon plants are planted in a narrow row 3.5° wide (½ the width of the triploid rows) between every second and third triploid row. For example, rows A and B are two consecutive rows of triploids, each 7-foot wide. Row C is a diploid row that is 3.5 feet wide. Row D and E are the following two 7 foot wide rows of triploids, followed by the 3.5-foot wide row F of diploid plants. This pattern is repeated across the width of the field. Because the diploid row is narrower according to the method of the invention, the distance between rows B and D is 10.5 feet instead of the traditional distance of 14 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

Example 2

Triploid watermelon plants are again planted in parallel rows 7 feet apart and 3 feet apart within each row. As in Example 1, the enhanced diploid watermelon plants are planted in a narrow row 3.5' wide, but are planted between every third and fourth triploid row. For example, rows A, B, and C, are three consecutive rows of triploids, each row being 7' wide. The following row D is a diploid row that is 3.5 feet wide. Row E, F, and G are the following three rows of triploids, all 7 feet wide, followed by a 3.5 foot wide row of enhanced pollenizer plants. This pattern is repeated across the width of the field. Because the diploid row is narrower according to the method of the invention, the distance between rows B and D is again 10.5 feet instead of the traditional distance of 14 feet. Using this ratio of 1 pollenizer row for every 3 triploid rows (1:3), 25% of the field would normally be used for the pollenizer plants. Reducing the width of the pollenizer row according to the method of the invention by one-half, the gain of space for planting additional triploid plants would be 25%/2 or approximately 12%.

Example 3

Triploid watermelons are planted in parallel rows 8 feet apart and 3 feet apart within each row. The enhanced diploid watermelon plants are planted in a narrow row 4.0 feet wide (½ the width of the triploid rows) between every second and third triploid row. For example, rows A and B are two consecutive rows of triploids, each 8 foot wide. Row C is a diploid row that is 4.0 feet wide. Row D and E are the following two 8 foot wide rows of triploids, followed by the 4.0 feet wide row F of diploid plants. This pattern is repeated across the width of the field. Because the diploid row is narrower according to the method of the invention, the distance between rows B and D is 12.0 feet instead of the traditional distance of 16 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

Example 4

Referring to the above three examples, when triploids are planted in rows 8 feet apart, and the ratio of diploid to triploid is 1:3, it is now clear that the reduction of the pollenizer row width by one-half will gain space for planting additional 12%.

Example 5

It is also within the scope of the invention to reduce the pollenizer row width to approximately ⅓ that of the triploid row width. Thus, according to the present invention, at any row width, when the ratio of diploid rows to triploid rows is:

(a.) 1:2, the savings of field area for additional triploid plants is (33%×⅔) or 22%.
(b) 1:3, the savings of field area for additional triploid plants is (25%×⅔) or 16.5%.
(c) 1:4, the savings of field area for additional triploid plants is (20%×⅔) or 13.2%.

It is also within the scope of the invention to reduce the pollenizer row width to approximately ⅔ that of the triploid row width.

Example 6

It is also within the scope of the present invention to inter-plant the diploid plants within the rows of triploid plants. According to the invention, the triploid plants are first planted by machine or by hand in regularly spaced rows. The triploid plants within each row are planted, for example, 3 feet apart. After the triploid plants are in the field as described, the diploid pollenizer watermelon plants of the invention are inter-planted, by hand, within each row approximately midway between the triploid plants, i.e. the diploid pollenizer watermelon plants of the invention are inserted between the triploid plants. Thus, in this example, the diploid plants are planted approximately 1.5 feet from the flanking triploid plants within the row. Due to the characteristics of the enhanced pollenizer of the invention, the diploid plants can be inter-planted within each row after every 2, 3, 4, 5, 6, 7, 8, 9, or 10 consecutive triploid plants. It is currently preferred in the industry to plant the diploid plants after every 2 (1:2) or 3 (1:3) triploid plants within the row. A 1:4 ratio has been reported, but is not normally used in commercial fields due to inadequate pollenization of the triploid plants. The field area saved under this example, when compared with both the current methods of planting diploids in separate rows or within a row at the ratios (diploid:triploid) of:

(a) 1:2, is 33.3%,
(b) 1:3, is 25%,
(c) 1:4, is 20%.

The enhanced pollenizer and method of the present invention comprises planting the enhanced pollenizer watermelons in rows that are narrower than the rows containing the triploid plants. Although the narrower diploid row will encourage diploid plant growth into the triploid plant row, the novel characteristics of the enhanced pollenizer watermelon allow it maintain its ability to sufficiently pollinate the triploid plants in the field. Thus, the enhanced pollenizer watermelon and method of the present invention increase the yield of seedless watermelon in a field.

Example 7

A split-plot design is used for this experiment to test three inbred enhanced pollenizers and three hybrid enhanced pollenizers against the commercial checks SANGRIA™ 2:1 and SANGRIA™ 3:1. All 6 enhanced pollenizers are inserted between regularly spaced (80"×24") triploid plants in the ratio of 3:1. For SANGRIA™ 2:1 ratio, every third space is a SANGRIA™ plant. For Sangria 3:1 ratio, every $4^{th}$ space is a SANGRIA™ plant. A 5:1 ratio is also included in this trial using the mixed enhanced pollenizers. In this treatment, the enhanced pollenizers plant is inserted between $5^{th}$ and $6^{th}$ regularly spaced triploid plants. So there are total 9 main plots, the 9 main treatments/pollinators, in this experiment. The 9 main plots are separated by cantaloupe plants. 3 different triploids, the sub-plots, with 2 replications are used to test different pollinators (see table 3). Plants are well grown except the leaf-miner damage. This damage results in smaller fruit size for Palomar and Tri-X-313. The trials are evaluated after about two months. The number of triploid fruit in each sub-plot is counted. The first 15 fruits in each sub-plot are non-selectively harvested and weighted. 10 fruits are also harvested from each pollinator and measured for rind firmness. Data are analyzed using S-Plus 6.1. The enhanced pollenizers varieties are also evaluated for fruit size and other fruit characteristics.

As shown in table 3, very similar fruit set per plant is achieved for all the pollenizer used. Smaller triploid seedless melons are produced when SANGRIA™ is used as pollinator in the ratio of 2:1 in this experiment. This could be due to SANGRIA™'s strong competition to the triploid plant for space, water and nutrient. A lot more seedless melons per acre, 25% (compared to the 3:1 ratio) to 33% (compared to the standard 2:1 ratio), are produced when enhanced pollenizers varieties are used as pollenizer.

The rind of enhanced pollenizer varieties of the present invention is much less durable compared to diploid pollenizer Sangria, as indicated by the force used to penetrate the rind using a fruit firmness tester (Fruit Firmness Tester FT02 of Wagner Instruments, Greenwich, Conn. 06836). Should the pollenizer not be harvested for its commercial value, its brittle rind allows the pollinator fruit to be destroyed during fruit harvest or soon thereafter. This is helpful for unloading the pollenizer plant and maintaining the flowering ability of the pollenizer plants for longer period of time. The brittle rind of the enhanced pollenizer also reduces the risk of carry-over into the next season, as a weed, since the fruit, and plant debris can be easily destroyed, after harvest of the triploid fruit.

Enhanced pollenizer plants flower about 7 days earlier than diploid SANGRIA™. Enhanced pollenizer plants produce more than twice many of branches compared to SANGRIA™. This allows enhanced pollenizer plants to produce more male flowers, thereby reducing the number of pollenizer plants needed. The vine of enhanced pollenizer plant is much thinner than regular diploid plants. The leaf size and leaf-lobe size of enhanced pollenizer are much smaller than those of SANGRIA™. All these make enhanced pollenizer much less competitive for light, water and fertilizer, compared to regular diploid watermelon.

Enhanced pollenizer plants are producing male flowers after the harvest of triploid seedless fruits. This gives the potential of having a second fruit set and multiple harvests of triploid seedless fruit with single planting. The male flowers open earlier in the morning compared to regular watermelons, especially in the cooler days.

TABLE 3

Seedless Watermelon Fruit Yields Produced by Using Different Pollenizer and Rind Firmness of Different Pollenizer

| Pollinator | Fruit/Plant | | | | Fruit/Acre | | | | Frt Wt (lbs) | | | | Rind Firmness (g/mm$^2$) |
|---|---|---|---|---|---|---|---|---|---|---|---|---|---|
| | Palomar | RWT8124 | TriX313 | Mean | Palomar | RWT8124 | TriX313 | Mean | Palomar | RWT8124 | TriX313 | Mean | |
| SP Hyb 5:1 | 2.00 | 3.60 | 2.15 | 2.58 | 6534 | 11652 | 6957 | 8381 | 13.6 | 6.0 | 15.4 | 11.6 | NA |
| SP1 | 2.05 | 3.55 | 1.95 | 2.53 | 6719 | 11661 | 6413 | 8265 | 12.2 | 5.7 | 14.6 | 10.8 | 121 |
| SP1 × SP3 | 2.00 | 3.60 | 2.15 | 2.58 | 6579 | 11752 | 7001 | 8444 | 13.2 | 6.0 | 14.9 | 11.3 | 139 |
| SP2 | 1.90 | 3.50 | 1.90 | 2.43 | 6258 | 11479 | 6137 | 7958 | 12.1 | 6.0 | 13.3 | 10.5 | 123 |
| SP2 × SP1 | 1.85 | 3.30 | 2.20 | 2.45 | 6004 | 10728 | 7106 | 7946 | 13.1 | 5.8 | 14.0 | 10.9 | 129 |
| SP3 | 1.90 | 3.40 | 1.55 | 2.28 | 6210 | 11170 | 5116 | 7499 | 12.8 | 6.0 | 14.1 | 11.0 | 133 |
| SP3 × SP2 | 1.90 | 3.60 | 2.05 | 2.52 | 6219 | 11649 | 6577 | 8149 | 12.5 | 5.8 | 13.9 | 10.7 | 129 |
| SANGRIA ™ 2:1 | 1.90 | 3.50 | 2.00 | 2.47 | 4086 | 7596 | 4375 | 5352 | 10.5 | 5.7 | 12.5 | 9.6 | 302 |
| SANGRIA ™ 3:1 | 1.95 | 3.35 | 1.95 | 2.42 | 4737 | 8248 | 4863 | 5949 | 12.4 | 5.6 | 12.9 | 10.3 | |
| Mean | 1.95 | 3.52 | 2.02 | 2.49 | 5770 | 10405 | 5946 | 7374 | 12.5 | 5.8 | 13.8 | 10.7 | 154 |

TABLE 3-continued

Seedless Watermelon Fruit Yields Produced by Using Different Pollenizer and Rind Firmness of Different Pollenizer

| Factor | P-value | P-value | P-value | P-value |
|---|---|---|---|---|
| Pollinator | 0.0239 | 0.0000 | 0.0000 | 0.0000 |
| Triploid | 0.0000 | 0.0000 | 0.0000 | |
| Pollinator * Triploid | 0.4121 | 0.0061 | 0.0029 | |
| Replication | 0.9372 | 0.8580 | 0.6310 | |

Example 8

Eight triploid varieties (see table 4) are transplanted on two 80" beds and spaced 24" apart. These two beds are located in the center of our regular hybrid evaluation block. A diploid hybrid bed is placed in each side of the two trial beds to eliminate the pollination factor. About 90 plants are transplanted for each variety. Two days later, each triploid plot is divided into 2 sub-plots and the enhanced pollenizer SP-1 plants of the present invention are inserted in one of the 2 sub-plots in the ratio of 3:1, for each of the 8 triploid varieties. This planting pattern allows 3260 triploid plants per acre. The 8 triploid varieties differ in fruit shape, size and maturity. About 10 weeks later, the first 30 fruits are non-selectively harvested from each sub-plot and are weighted using a digital scale. Data are analyzed using S-Plus 6.1.

As shown in table 4, the fruit size differences are solely due to triploid variety differences. Inserting of enhanced pollenizer SP-1 between regularly spaced triploid plants in the ratio of 3:1 does not reduce the fruit size of triploid seedless fruit, regardless of the type of triploid variety. The triploid varieties used in this trial represent a very broad spectrum of triploids used in commercial production. They differ in fruit size, fruit shape, and maturity. Thus, inserting enhanced pollenizer plants of the present invention between regularly spaced triploid plants does not reduce the fruit size of the triploid seedless melons. Therefore, a seedless grower can plant his or her fields solid with triploid plants and then insert the enhanced pollenizer plants in a ratio of 3:1 or less. This planting pattern and ratio allows growers to produce significant higher (25 to 33%) yields of seedless fruit per acre.

TABLE 4

Effect of Inserting Super-Pollenizer Between Regularly Spaced (80" x 24") Triploid Plants in the Ratio of 3:1 to the Fruit Size of Eight Different Triploid Watermelon Varieties

| | Super-Pollenizer Insertion | | |
|---|---|---|---|
| Triploid Variety | No | Yes | Mean |
| 3X SANGRIA ™ | 18.05 | 18.51 | 18.28 |
| Palomar | 14.23 | 16.21 | 15.22 |
| RWT8126 | 16.97 | 17.15 | 17.06 |
| RWT8124 | 6.26 | 6.03 | 6.15 |
| RWT8139 | 15.46 | 14.43 | 14.94 |
| RWT8140 | 15.31 | 15.73 | 15.52 |
| Shadow | 15.97 | 14.73 | 15.35 |
| Tri-X-313 | 15.77 | 15.60 | 15.69 |
| Mean | 14.75 | 14.80 | 14.77 |

| Factor | P-Value |
|---|---|
| Triploid Variety | 0.0000 |
| Super-Pollenizer | 0.8829 |
| Variety * Super-Pollenizer | 0.2451 |

Example 9

Production of Dihaploid Watermelon Plants

Anthers of SP-1 plants were gamma-ray irradiated with cobalt 60 for a dose of 0.4 KGy. Irradiated pollen was gently transferred from the anthers to the receptive stigma on or before anthesis. Each ovary of the pollinated female received an application of 50 ppm CPPU (a plant cytokinin hormone) to stimulate fruit development. Plants were monitored for pollination take and fruit development. Fruit was harvested 14 days or 21 days post-pollination.

Harvested immature fruit were carefully cut open under sterile conditions and the seeds were meticulously removed from the flesh. The distal portion of each seed was cut off before plating about 40 seeds to each plate of culture medium. Sealed plates with seeds were cultured at 25° C. with a 16-hour photoperiod in a culture room on a Murashige and Skoog Basal Medium, 30 g/L sucrose, 10 g/L agar supplemented either with 10 µM BA (2.25 mg/L) or 22.2 µM BA (5 mg/L) and 2.85 µM IAA (0.5 mg/L), pH 5.8 and dispensed into 100×15 petri dishes after autoclaving.

After 30 days, seeds were screened for greenish immature embryos for embryo rescue. Those with embryos were moved to fresh medium. As the embryos germinated and elongated, they were transferred to small culture jars with the same medium. When sufficient leaf tissue was present on the plantlet, a leaf was sampled and ploidy analysis was carried out by flow cytometry.

Once the plantlets had been confirmed haploid, cuttings/clones are made and rooted in vitro. The medium consisted of half strength MS basal salts, 20 g/L sucrose, 1.0 µM IBA (0.2 mg/L), 4 g/L agar and 1 g/L Phytagel, pH 5.8. Once a good root system had developed, plantlets are moved into the greenhouse and planted in trays. The chromosome doubling occurred in the greenhouse by applying 58 µM Surflan (oryzalin) to all apical and axillary nodes. Once plants were established and new flowers exhibited the presence of pollen confirming restored fertility, they were self-pollinated and seed was harvested. Further increase of the dihaploid SP-1 can be done in a field isolated from any other watermelon plant, or physically isolated in a net cage.

Example 10

Measurements of Brittleness of Fruits

Watermelon plants of SP-1 and SANGRIA™ were sown at the Naples, Fla. research station on Aug. 7, 2003 and transplanted to open field on Sep. 9, 2003. Fruits were harvested from the plants on Nov. 20, 2003. Mature fruits were tested using a Tester FT327 of Wagner Instruments, Greenwich, Conn. 06836 and a 3.0 mm tip. Ten fruits of SP-1 and SANGRIA™ were tested. The average pressure to puncture the rind of fruits of SP-1 was 3 lb 8 oz (1,587 g). The average pressure to puncture the rind of fruits of SANGRIA™ was 11 lb 6 oz (5,159 g).

Example 11

Measurements of Brittleness of Fruits

Watermelon plants of SP-1 and SANGRIA™ were grown at the Naples, Fla. research station. Fruits were harvested on Dec. 4, 2003 from plants about 17 weeks after sowing. Mature fruits (about 35-40 days after anthesis) were tested. The fruits were tested in the morning at about 9 to 10 am. Different models of Wagner penetrometers (Tester FT327, a Tester FT011 or a Tester FT02 of Wagner Instruments, Greenwich, Conn. 06836) were used in combination with a 2 mm or a 3 mm tip. The tip of the penetrometer was placed vertically on the top surface of the fruit in the middle portion of the fruit. For SP-1, 5 fruits (1 to 5) were tested in three independent measurements (A, B, C). For SANGRIA™, one fruit was tested in three independent measurements (A, B, C). The results are shown in Table 5A (2 mm tip) and Table 5B (3 mm tip).

TABLE 5A

| SP-1 | FT02/2 mm (force in g) | | | | FT327/2 mm (force in g) | | | | FT011/2 mm (force in g) | | | |
|---|---|---|---|---|---|---|---|---|---|---|---|---|
| | A | B | C | Average per fruit | A | B | C | Average per fruit | A | B | C | Average per fruit |
| Fruit 1 | 1450 | 1460 | 1520 | 1477 | 1700 | 1300 | 1350 | 1450 | 1650 | 1250 | 1300 | 1400 |
| 2 | 1120 | 1000 | 1220 | 1113 | 1100 | 1100 | 1200 | 1133 | 1700 | 1200 | 1150 | 1350 |
| 3 | 970 | 990 | 1370 | 1110 | 1750 | 1000 | 1200 | 1317 | 1100 | 1100 | 1150 | 1117 |
| 4 | 1150 | 1140 | 1100 | 1130 | 1400 | 1100 | 1200 | 1233 | 1000 | 1150 | 1100 | 1083 |
| 5 | 1150 | 1190 | 1270 | 1203 | 1200 | 1200 | 1100 | 1167 | 1200 | 1150 | 950 | 1100 |
| Average all fruits | | | | 1207 | | | | 1260 | | | | 1210 |
| (std dev all fruits) | | | | (175) | | | | (216) | | | | (208) |
| SANGRIA ™ 1 | not able to break through rind | | | | 3500 | 2900 | 3500 | 3300 | 3350 | 3750 | 3150 | 3417 |
| (std dev) | | | | | | | | (346) | | | | (306) |

TABLE 5B

| SP-1 | FT02/3 mm (force in g) | | | | FT327/3 mm (force in g) | | | | FT011/3 mm (force in g) | | | |
|---|---|---|---|---|---|---|---|---|---|---|---|---|
| | A | B | C | Average per fruit | A | B | C | Average per fruit | A | B | C | Average per fruit |
| Fruit 1 | 2240 | 1950 | 2250 | 2147 | 1900 | 2100 | 2100 | 2033 | 1850 | 2000 | 2200 | 2017 |
| 2 | 1720 | 1690 | 1720 | 1710 | 1600 | 1700 | 1800 | 1700 | 1800 | 1800 | 1700 | 1767 |
| 3 | 1910 | 2000 | 2100 | 2003 | 1700 | 1600 | 1800 | 1700 | 1750 | 1550 | 1650 | 1650 |
| 4 | 1910 | 1970 | 1900 | 1927 | 1900 | 1800 | 1800 | 1833 | 1550 | 1650 | 1750 | 1650 |
| 5 | 1930 | 1840 | 1880 | 1883 | 1900 | 1900 | 1800 | 1867 | 1600 | 1700 | 1700 | 1667 |
| Average all fruits | | | | 1934 | | | | 1827 | | | | 1750 |
| (std dev all fruits) | | | | (167) | | | | (149) | | | | (171) |
| SANGRIA ™ 1 | not able to break through rind | | | | 4200 | 5400 | 4800 | 4800 | 5000 | 5000 | 5200 | 5067 |
| (std dev) | | | | | | | | (600) | | | | (115) |

TABLE 6

| | Force in Grams (Pounds) 3 mm Tip (FT 30M) | Force in Grams (Pounds) 2 mm Tip (FT 20M) |
|---|---|---|
| SP-1 | 1452 (3.2) | 680 (1.5) |
| | 1270 (2.8) | 726 (1.6) |
| | 1452 (3.2) | 680 (1.5) |
| | 1633 (3.6) | 1043 (2.3) |
| | 1043 (2.3) | 590 (1.3) |
| | 1043 (2.3) | 771 (1.7) |
| | 1588 (3.5) | 816 (1.8) |
| | 1542 (3.4) | 998 (2.2) |
| | 1633 (3.6) | 907 (2.0) |
| | 1588 (3.5) | 454 (1.0) |
| | 1678 (3.7) | 816 (1.8) |
| AVE | 1447 (3.2) | 771 (1.7) |
| STD | 179 (0.4) | 132 (0.3) |
| SANGRIA ™ | 4763 (10.5) | 2903 (6.4) |
| | 5670 (12.5) | 2903 (6.4) |
| | 6804 (15.0) | 3992 (8.8) |
| | 4717 (10.4) | 3175 (7.0) |
| | 7439 (16.4) | 4082 (9.0) |
| | 5171 (11.4) | 2631 (5.8) |
| | 5352 (11.8) | 2722 (6.0) |
| | 5534 (12.2) | 2722 (6.0) |
| | 5897 (13.0) | 3175 (7.0) |
| | 6350 (14.0) | 3266 (7.2) |
| AVE | 5770 (12.7) | 3157 (7.0) |
| STD | 682 (1.5) | 381 (0.8) |

Example 12

Measurements of Brittleness of Fruits

Watermelon plants of SP-1 and SANGRIA™ were sown on Jan. 16, 2004 at the Naples, Fla. station. Fruits were harvested on May 17, 2004 and tested using Tester FT 327 (Wagner Instruments, Greenwich, Conn. 06836) in combination with a 2 mm or a 3 mm tip. Ten mature fruit of SP-1 and SANGRIA™ were tested, and the results are shown in Table 6.

Deposit

Applicants have made a deposit of at least 2500 seeds of enhanced watermelon pollenizer line NO1F3203B (now called SP-1) with the American Type Culture Collection (ATCC), Manassas, Va., 20110-2209 U.S.A., ATCC Deposit No: PTA-4856. This deposit of the enhanced watermelon pollenizer line NO1F3203B/SP-1 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims. Thus, although the foregoing invention has been described in some detail in this document, it will be obvious that changes and modification may be practiced within the scope of the invention, as limited only by the scope of the appended claims.

All references cited herein are incorporated by reference in the application in their entireties.

What is claimed is:

1. A watermelon plant comprising, at maturity:
    a) a fruit, the rind of which breaks under a pressure of not more than about 1,800 g when a fruit tester with a 2 mm tip is used or under a pressure of not more than about 2,300 g when a fruit tester with a 3 mm tip is used; and
    b) a 5th leaf from the smallest new leaf on a vine having a surface area of not more than about 50 $cm^2$;

wherein said plant is produced by crossing a watermelon plant with a plant of NO1F3203B deposited under Accession No. PTA-4856; obtaining a progeny; and selecting for characteristics set forth in a) and b).

2. The watermelon plant of claim 1, wherein the rind of said fruit breaks under a pressure in the range of about 400 g to about 1,800 g when a fruit tester with a 2 mm tip is used.

3. The watermelon plant of claim 1, wherein said 5th leaf has a surface area in the range of about 15 $cm^2$ to about 50 $cm^2$.

4. The watermelon plant of claim 1, wherein the weight of said fruit is in the range of about 2 lbs to about 7 lbs.

5. A seed that produces the plant of claim 1.

* * * * *